United States Patent [19]

Ellefson et al.

[11] 4,123,430

[45] Oct. 31, 1978

[54] 2-ARYL-4-(1-PIPERAZINYL)-3H-1,5-BENZODIAZEPINES

[75] Inventors: Charles R. Ellefson, Chicago; Fred M. Hershenson, Morton Grove, both of Ill.

[73] Assignee: G. D. Searle & Co., Chicago, Ill.

[21] Appl. No.: 850,438

[22] Filed: Nov. 10, 1977

[51] Int. Cl.² .................... C07D 295/12; C07D 403/04
[52] U.S. Cl. ..................................... 260/243.3; 424/250
[58] Field of Search ....................... 260/268 BC, 243.3

[56] References Cited

U.S. PATENT DOCUMENTS

| 2,957,867 | 10/1960 | Werner | 260/268 BC |
| 3,933,793 | 1/1976 | Nardi et al. | 260/268 BC |
| 3,998,809 | 12/1976 | Milkowski et al. | 260/268 BC |

FOREIGN PATENT DOCUMENTS 481,128  12/1969  Switzerland.

OTHER PUBLICATIONS

Matsumoto et al., Bull. Chem. Soc. Japan, vol 43, pp. 1496–1500 (1970).
Ried et al., Liebigs Ann. Chem., 755, pp. 24–31 (1972).
Hunter et al., Tetrahedron, vol 29, pp. 147–153 (1973) & vol. 28, pp. 5573–5581 (1972).
Muller et al., Chem. Ber., vol 106, pp. 332–338 (1973).

*Primary Examiner*—Paul M. Coughlan, Jr.
*Attorney, Agent, or Firm*—Dragan J. Karadzic

[57] ABSTRACT

2-Aryl-4-(1-piperazinyl)-3H-1,5-benzodiazepines of the formula

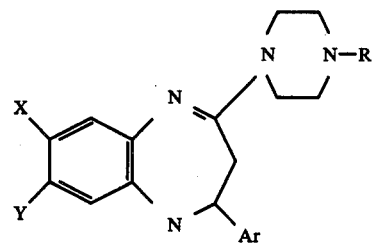

wherein R is hydrogen, alkyl having from 1 to 7 carbon atoms or phenyl; Ar is phenyl, trifluoromethylphenyl or phenyl substituted with 1 or 2 halogen, alkyl having from 1 to 4 carbon atoms or alkoxy having from 1 to 4 carbon atoms; X and Y are each hydrogen, halogen, alkyl having from 1 to 4 carbon atoms or alkoxy having from 1 to 4 carbon atoms; and the dotted line represents a single bond wherein hydrogen is attached to N or a double bond. These compounds are useful as muscle relaxants.

15 Claims, No Drawings

2-ARYL-4-(1-PIPERAZINYL)-3H-1,5-BENZODIAZEPINES

The present invention relates to 2-aryl-4-(1-piperazinyl)-3H-1,5-benzodiazepines having the following general formula

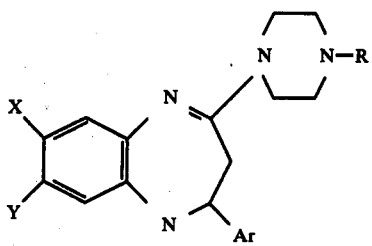

wherein R is hydrogen, alkyl having from 1 to 7 carbon atoms or phenyl; Ar is phenyl, trifluoromethylphenyl or phenyl substituted with 1 or 2 halogen, alkyl having from 1 to 4 carbon atoms or alkoxy having from 1 to 4 carbon atoms; X and Y are each hydrogen, halogen, alkyl having from 1 to 4 carbon atoms or alkoxy having from 1 to 4 carbon atoms; and the dotted line represents a single bond wherein hydrogen is attached to N or a double bond.

The alkyls comprehended by R are methyl, ethyl, propyl, butyl, pentyl, hexyl, heptyl and the branched-chain isomers thereof, with methyl being preferred.

The alkoxy radicals comprehended by substituents X and Y are methoxy, ethoxy, propoxy, butoxy, pentoxy, hexyloxy, heptyloxy and the branched-chain isomers thereof, with methoxy preferred.

The halogens comprehended by X and Y and as substituents on the phenyl are bromine, chlorine, fluorine and iodine, with fluorine and chlorine being preferred.

The alkyls of 1 to 4 carbon atoms comprehended by substituents X and Y and as substituents on the phenyl are methyl, ethyl, propyl, butyl and the branched-chair isomers thereof with methyl being preferred.

The alkoxy radicals comprehended as substituents on the phenyl are methoxy, ethoxy, propoxy, butoxy, and the branched-chain isomers thereof with mehtoxy being preferred.

Positioning of the substituents on the phenyl relative to the point of attachment of the phenyl, or where two are present, to each other is not critical. Thus, within the scope of this invention are o-, m-, or p-monosubstituted phenyls of the type described above, such as o-fluorophenyl, p-chlorophenyl, p-tolyl, p-methoxyphenyl, m-trifluoromethylphenyl and p-fluorophenyl and 2,3-, 2,4- 2,5-, 2,6-, 3,4-, and 3,5-disubstituted phenyls of the type described above, such as 2,4-dichlorophenyl, 2,6-dimethoxyphenyl, 2,3-difluorophenyl, 3,4-dimethylphenyl, 3-chloro-5-fluorophenyl and 2-fluoro-5-methylphenyl.

Embodiments of the present invention of the formula

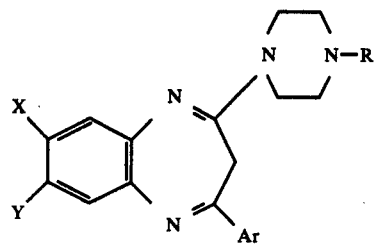

wherein R, X, Y and Ar are as previously defined are preferred embodiments and of these embodiments compounds of the formula

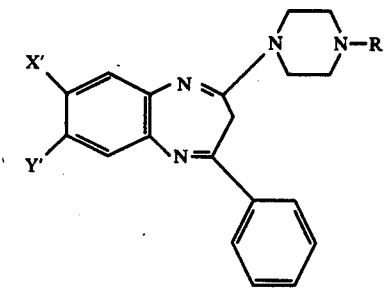

wherein R is as previously defined; X' is hydrogen, halogen or alkyl having from 1 to 7 carbon atoms; and Y' is hydrogen, halogen or alkyl having from 1 to 7 carbon atoms are further preferred.

Other preferred embodiments of this invention are compounds of the formula

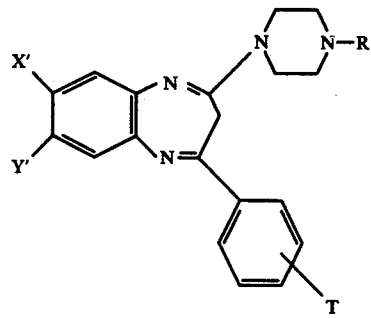

wherein R, X' and Y' are are as previously defined; and T is halogen, alkyl having from 1 to 4 carbon atoms or alkoxy having from 1 to 4 carbon atoms and of these embodiments compounds of the formula

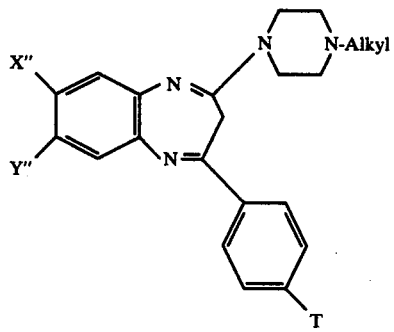

wherein T is as previously defined; X" and Y" are each hydrogen or alkyl having from 1 to 7 carbon atoms; and Alkyl contains from 1 to 7 carbon atoms are particularly preferred.

The compounds of the present invention are useful because of their pharmacological properties. In particular, they are useful as muscle relaxants. Muscle relaxants are known to cause skeletal muscular relaxation without loss of consciousness as a result of a selective action upon the CNS. They have established value in treating acute muscle spasms associated with trauma and inflammation. They are also beneficial in producing muscle relaxation for certain orthopedic manipulations.

The muscle relaxant activity of the present compounds is demonstrated in the well known traction wire test. This test measures the ability of mice to stay on a horizontal traction wire (12 long × 2/16 inch in diameter) for 40 seconds. Control mice have no difficulty staying on the traction wire for this period of time. Male Crl: COBS CD-1(ICR)BR mice weighing 20–30 grams are used. Each compound is tested at five dose levels (typically 20, 40, 80, 160 and 320 mg/kg in groups of 6 to 10 mice per dose level. A test compound is suspended in saline containing approximately 2% by volume of a 50:50 mixture of propylene glycol and polysorbate-80 and administered intraperitoneally or intragastrically to groups of 6 to 10 mice. One-half, one, two, and 24 hours after the administration, the mice are placed on the traction wire and the number of mice falling off within 40 seconds is recorded. A test compound is considered active if 50% or more of the drug treated mice fall from the wire.

Representative compounds of the present invention, 2-(p-methoxyphenyl)-4-(4-methyl-1-piperazinyl)-3H-1,5-benzodiazepine, 4-(4-methyl-1-piperazinyl)-2-(p-tolyl)-3H-1,5-benzodiazepine, 2-(p-fluorophenyl)-7,8-dimethyl-4-(4-methyl-1-piperazinyl)-3H-1,5-benzodiazepine and 1,2-dihydro-5-(4-methyl-1-piperazinyl)-2-phenyl-3H-1,5-benzodiazepine are found active in the above test at a dose of 20–80 mg/kg at one-half and one hour periods, and 40 mg/kg at two hours period.

Compounds of the present invention are conveniently prepared by reacting a 2-alkylthio-5-aryl-3H-1,5-benzodiazepine of the formula

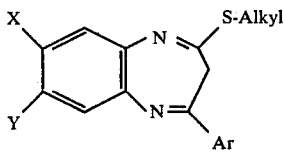

wherein Ar, Alkyl, X and Y are as previously defined, with a piperazine of the formula

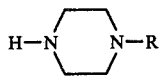

wherein R is as previously defined, in the presence of glacial acetic acid in an inert organic solvent such as toluene, benzene or chloroform and subsequently hydrogenating thus obtained compound to produce 1,2-dihydro compounds of this invention.

The 2-alkylthio-4-aryl-3H-1,5-benzodiazepine starting materials are prepared according to the procedure of D. Nardi et. al., J. Heterocycl. Chem., 10 (5), 815–19 (1973) set out in Scheme I.

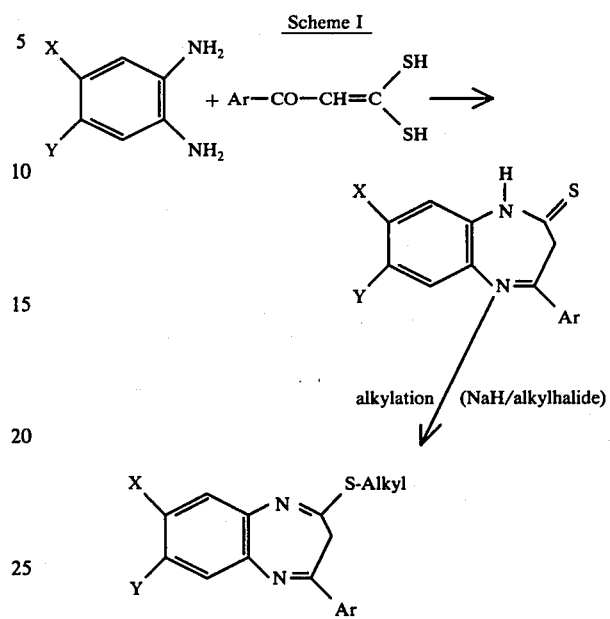

Alternatively, the 2-alkyl-4-aryl-3H-1,5-benzodiazepine starting materials are prepared by the thiation of 4-aryl-1,3-dihydro-2H-1,5-benzodiazepin-2-ones [prepared according to the procedure described by W. Reed and P. Stahlhofen, Chem. Ber. 90, 828 (1957)] as set out in Scheme II.

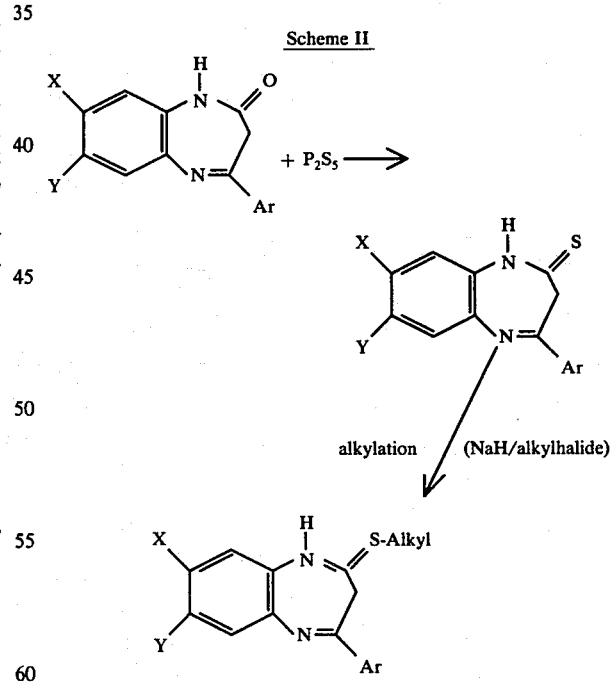

2,3-Dihydro-2-phenyl-4-(1-piperazinyl and 4-methyl-1-piperazinyl)-1,5-benzothiazepine are disclosed in Swiss Patent No. 481,128 and by O. Hideg-Hankovszky and K. Hideg, Acta. Chim. (Budapest), 68 (4), 403–10 (1971), respectively. Compounds of the present invention are particularly distinct from the above two compounds in that they are benzodiazepine derivatives and from the second compound in addition by virtue of the piperazinyl substituent.

2,3-Dihydro-2,4-diphenyl-1H-1,5-benzodiazepine and various 2-aryl-4-phenyl-3H-1,5-benzodiazepines are described by P. Hunter and G. Webb, Tetrahedron, 28, 5573-81 (1972), and M. Matsumoto, et. al., Bull. Chem. Soc. Jap. 43 (5), 1496–500 (1970), W. Ried and E. Koenig, Liebigs Ann. Chem., 755, 24—31 (1973), W. Mueller et. al., Chem. Ber., 106, 332–38 (1973), and S. Korshunov et. al., Khim. Geterotsikl. Soedin., 10, 1421–2 (1973), respectively. Compounds of the present invention are particularly distinct from the aforementioned compounds by virtue of the optionally substituted 1-piperazinyl substituent.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth temperatures are given in degrees Centigrade (° C), and relative amounts in parts by weight, unless parts by volume is specified. The relationship between parts by weight and parts by volume is the same as that existing between grams and milliliters.

EXAMPLE 1

To a refluxing solution of 16.2 parts of o-phenylenediamine in 100 parts by volume of xylene is added dropwise over a one hour period a solution of 28.8 parts of ethyl benzoylacetate in 100 parts by volume of xylene. The solvent is then partially distilled off and the concentrated reaction solution is cooled. The crystalline residue which forms on cooling is separated by filtration. The residue is 2,3-dihydro-5-phenyl-1H-1,5-benzodiazepin-2-one. This compound has the formula

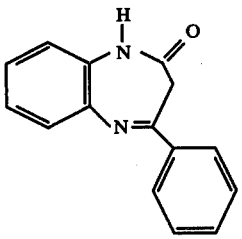

Use of equivalent quantities of the appropriate o-phenylenediamine and the appropriate ethyl aroylacetate in the above detailed procedure affords the following compounds:
2,3-dihydro-7,8-dichloro-4-phenyl-1H-1,5-benzodiazepin-2-one;
2,3-dihydro-4-(3,4-dichlorophenyl)-1H-1,5-benzodiazepin-2-one;
2,3-dihydro-4-(2,5-dimethylphenyl)-1H-1,5-benzodiazepin-2-one;
2,3-dihydro-4-(2,6-dimethoxyphenyl)-1H-1,5-benzodiazepin-2-one; and
2,3-dihydro-7,8-dimethoxy-4-phenyl-1H-1,5-benzodiazepin-2-one.

EXAMPLE 2

A mixture of 23.6 parts of 2,3-dihydro-4-phenyl-1H-1,5-benzodiazepin-2-one and 24.4 parts of phosphorus pentasulfide in 400 parts by volume of pyridine is stirred at reflux temperature for one hour. This solution is then added dropwise with stirring to about 2000 parts by volume of 60° C. warm water. The solid which forms is separated by filtration, washed with water and dried in air overnight. The product thus obtained is recrystallized from ethyl acetate to give, as beige crystals, 2,3-dihydro-4-phenyl-1H-1,5-benzodiazepine-2-thione. This product has the formula

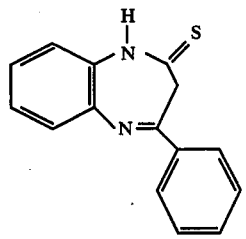

Use of an equivalent quantity of the appropriate 1H-1,5-benzodiazepin-2-one in the above detailed procedure affords the following compounds:
2,3-dihydro-7,8-dichloro-4-phenyl-1H-1,5-benzodiazepine-2-thione;
2,3-dihydro-4-(3,4-dichlorophenyl)-1H-1,5-benzodiazepine-2-thione;
2,3-dihydro-4-(3,5-dimethylphenyl)-1H-1,5-benzodiazepine-2-thione;
2,3-dihydro-4-(3,4-dimethoxyphenyl)-1H-1,5-benzodiazepine-2-thione; and
2,3-dihydro-7,8-dimethoxy-4-phenyl-1H-1,5-benzodiazepine-2-thione.

EXAMPLE 3

109 Parts of tertiary amyl alcohol is added dropwise with stirring to a suspension of 52 parts of 57% sodium hydride in 750 parts by volume of dry benzene. After the addition is completed, the reaction mixture is stirred at reflux temperature until the evolution of hydrogen gas ceases. The reaction mixture is then cooled in an ice bath and filtered. A solution of 75 parts of acetophenone and 94 parts of carbon disulfide is added dropwise with stirring to the filtrate. The reaction mixture is stirred for an additional hour and then left standing at room temperature overnight. Water is then added to the mixture and the aqueous layer separated from the benzene layer. The benzene layer is washed with water and these washes are combined with the aqueous layer. The combined aqueous layer is acidified with 10% sulfuric acid. The solid which precipitates is extracted into ether, the ether extract washed with water and dried over anhydrous magnesium sulfate. After removal of the ether, the residue is washed with n-hexane to give, as an orange powder 3,3-dimercaptoacrylophenone. This compound has the formula

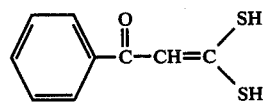

Substitution of an equivalent quantity of the appropriate acetophenone in the above detailed procedure and substantial repetition of that procedure affords the following compounds:
4'-chloro-3,3-dimercaptoacrylophenone;
4'-fluoro-3,3-dimercaptoacrylophenone;

3,3-dimercapto-4'-methoxyacrylophenone;
3,3-dimercapto-4'-methylacrylophenone; and
3,3-dimercapto-4'-(trifluoromethyl)-acrylophenone.

EXAMPLE 4

A mixture of 6.8 parts of 4,5-dimethyl-o-phenylenediamine and 9.8 parts of 3,3-dimercaptoacrylophenone in 200 parts by volume of xylene is stirred at 110°–130° C. for about 150 minutes and then left standing at room temperature overnight. The crystalline solid which forms is separated by filtration, washed with several portions of n-hexane and air dried to give light beige crystals. These crystals are dissolved in boiling ethyl acetate, the solution is concentrated, and cooled giving off-white crystals melting at about 215.5°–218° C. This crystalline product is 2,3-dihydro-7,8-dimethyl-4-phenyl-1H-1,5-benzodiazepine-2-thione. The product has the formula

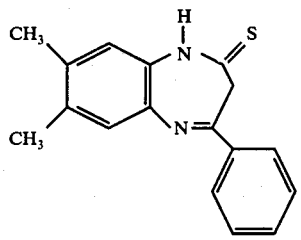

Substituting equivalent quantities of the appropriate o-phenylenediamine and the appropriate 3,3-dimercaptoacrylophenone for 4,5-dimethyl-o-phenylenediamine and 3,3-dimercaptoacrylophenone called for respectively in the above detailed procedure and substantially repeating that procedure the following compounds are obtained:
8-chloro-2,3-dihydro-4-phenyl-1H-1,5-benzodiazepine-2-thione;
4-(p-chlorophenyl)-2,3-dihydro-1H-1,5-benzodiazepine-2-thione;
4-(p-fluorophenyl)-2,3-dihydro-1H-1,5-benzodiazepine-2-thione;
2,3-dihydro-4-(p-methoxyphenyl)-1H-1,5-benzodiazepine-2-thione;
2,3-dihydro-4-(p-tolyl)-1H-1,5-benzodiazepine-2-thione;
4-(p-fluorophenyl)-2,3-dihydro-7,8-dimethyl-1H-1,5-benzodiazepine-2-thione;
7,8-difluoro-2,3-dihydro-4-phenyl-1H-1,5-benzodiazepine-2-thione;
7-chloro-4-(p-chlorophenyl)-2,3-dihydro-8-methyl-1H-1,5-benzodiazepine-2-thione;
2,3-dihydro-8-methoxy-4-phenyl-1H-1,5-benzodiazepine-2-thione;
2,3-dihydro-8-methyl-4-(p-trifluoromethylphenyl)-1H-1,5-benzodiazepine-2-thione; and
2,3-dihydro-8-methyl-4-(p-tolyl)-1H-1,5-benzodiazepine-2-thione.

EXAMPLE 5

12.6 parts of 2,3-dihydro-4-phenyl-1H-1,5-benzodiazepine-2-thione is suspended in 1000 parts by volume of dry benzene. To this suspension is added 3 parts of 57% sodium hydride and the resultant mixture is stirred for about 2 hours at reflux temperature. 10 Parts of methyl iodide is then added to the reaction mixture and stirring is continued at reflux temperature overnight. The reaction mixture is then cooled to room temperature, filtered and the filtrate concentrated under reduced pressure to afford 2-methylthio-4-phenyl-3H-1,5-benzodiazepine, as an oil. This compound has the formula

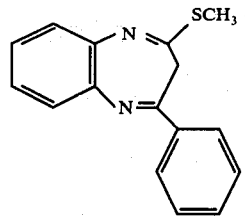

Substitution of an equivalent quantity of the appropriate 2,3-dihydro-4-aryl-1H-1,5-benzodiazepine-2-thione for 2,3-dihydro-4-phenyl-1H-1,5-benzodiazepine-2-thione called for in the above detailed procedure and substantial repetition of that procedure affords the following compounds:
7,8-dichloro-2-methylthio-4-phenyl-3H-1,5-benzodiazepine;
4-(3,4-dichlorophenyl)-2-methylthio-3H-1,5-benzodiazepine;
4-(3,5-dimethylphenyl)-2-methylthio-3H-1,5-benzodiazepine;
4-(3,4-dimethoxyphenyl)-2-methylthio-3H-1,5-benzodiazepine;
7,8-dimethoxy-2-methylthio-4-phenyl-3H-1,5-benzodiazepine;
7,8-dimethyl-2-methylthio-4-phenyl-3H-1,5-benzodiazepine;
8-chloro-2-methylthio-4-phenyl-3H-1,5-benzodiazepine;
4-(p-chlorophenyl)-2-methylthio-3H-1,5-benzodiazepine;
4-(p-fluorophenyl)-2-methylthio-3H-1,5-benzodiazepine;
4-(p-methoxyphenyl)-2-methylthio-3H-1,5-benzodiazepine;
2-methylthio-4-(p-tolyl)-3H-1,5-benzodiazepine;
4-(p-fluorophenyl)-7,8-dimethyl-2-methylthio-3H-1,5-benzodiazepine;
7,8-difluoro-2-methylthio-4-phenyl-3H-1,5-benzodiazepine;
7-chloro-4-(p-chlorophenyl)-2-methylthio-3H-1,5-benzodiazepine;
8-methoxy-2-methylthio-4-phenyl-3H-1,5-benzodiazepine;
8-methyl-2-methylthio-4-(p-trifluoromethylphenyl)-3H-1,5-benzodiazepine; and
8-methyl-2-methylthio-4-(p-tolyl)-3H-1,5-benzodiazepine.

EXAMPLE 6

A solution of 13.3 parts of 2-methylthio-4-phenyl-3H-1,5-benzodiazepine, 26 parts by volume of 1-methylpiperazine and 1.5 part of glacial acetic acid in 150 parts by volume of chloroform is stirred at reflux temperature overnight. The solvent is then removed under reduced pressure and the residue partititoned between water and benzene. The benzene portion is washed with water and then extracted with 10% acetic acid. The acidic extract is washed with benzene and then made alkaline with concentrated ammonia. The alkaline mixture is extracted with benzene, the benzene extract washed with water and then dried over anhydrous magnesium sulfate. After the solvent is removed a crude yellow solid is obtained. The crude solid is recrystallized from a mixture of chloroform and n-hexane to yield 4-(4-methyl-1-piperazinyl)-2-phenyl-3H-1,5-benzodiazepine, melting at about 155°–157° C. This compound has the following formula

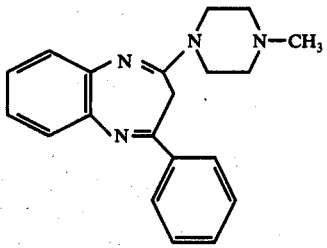

Substitution of equivalent quantities of the appropriate 2-methylthio-4-aryl-3H-1,5-benzodiazepine and 1-alkylpiperazine for 2-methylthio-4-phenyl-3H-1,5-benzodiazepine and 1-methylpiperazine called for in the above detailed procedure and substantial repetition of that procedure affords the following compounds:

7-chloro-4-(4-methyl-1-piperazinyl)-2-phenyl-3H-1,5-benzodiazepine, melting at about 125.5°–126.5° C.;
7,8-dimethyl-4-(4-methyl-1-piperazinyl)-2-phenyl-3H-1,5-benzodiazepine, melting at about 131.5°–134.5° C.;
2-phenyl-4-(4-phenyl-1-piperazinyl)-3H-1,5-benzodiazepine, melting at about 172°–172.5° C.;
2-(p-chlorophenyl)-4-(4-methyl-1-piperazinyl)-3H-1,5-benzodiazepine, melting at about 155.5°–157.5° C.;
2-(p-fluorophenyl)-4-(4-methyl-1-piperazinyl)-3H-1,5-benzodiazepine, melting at about 157°–158° C.;
2-(p-methoxyphenyl)-4-(4-methyl-1-piperazinyl)-3H-1,5-benzodiazepine, melting at about 148.5°–150° C.;
4-(4-methyl-1-piperazinyl)-2-(p-tolyl)-3H-1,5-benzodiazepine melting at about 129.5°–132° C.;
2-(p-fluorophenyl)-7,8-dimethyl-4-(4-methyl-1-piperazinyl)-3H-1,5-benzodiazepine, melting at about 169°–170° C.;
7,8-dichloro-2-phenyl-4-(1-piperazinyl)-3H-1,5-benzodiazepine;
7,8-difluoro-2-phenyl-4-(4-ethyl-1-piperazinyl)-3H-1,5-benzodiazepine;
2-(p-chlorophenyl)-8-chloro-7-methyl-4-(4-methyl-1-piperazinyl)-3H-1,5-benzodiazepine;
7-methoxy-4-(4-methyl-1-piperazinyl)-2-phenyl-3H-1,5-benzodiazepine;
7,8-dimethoxy-2-phenyl-4-(4-propyl-1-piperazinyl)-3H-1,5-benzodiazepine;
2-(3,4-dichlorophenyl)-4-(4-methyl-1-piperazinyl)-3H-1,5-benzodiazepine;
7-methyl-4-(1-piperazinyl)-2-(p-trifluromethyl-phenyl)-3H-1,5-benzodiazepine;
2-(3,5-dimethylphenyl)-4-(4-methyl-1-piperazinyl)-3H-1,5-benzodiazepine;
2-(3,4-dimethoxyphenyl)-4-(4-methyl-1-piperazinyl)-3H-1,5-benzodiazepine;
7-methyl-4-(4-phenyl-1-piperazinyl)-2-(p-tolyl)-3H-1,5-benzodiazepine; and
2-phenyl-4-(1-piperazinyl)-3H-1,5-benzodiazepine.

EXAMPLE 7

To a solution of 5 parts of 4-(4-methyl-1-piperazinyl-2-phenyl-3H-1,5-benzodiazepine in 100 parts by volume of dioxane is added 2 parts of 5% palladium-on-carbon catalyst and the resulting mixture is shaken with hydrogen at 2 psi pressure and room temperature until 1 molecular equivalent of hydrogen is absorbed. The catalyst is then removed by filtration and the solvent distilled off under reduced pressure from the filtrate leaving a clear oil which crystallizes on standing. The crude crystals are recrystallized from a mixture of ethyl acetate and n-hexane to affor 2,3-dihydro-4-(4-methyl-1-piperazinyl)-2-phenyl-1H-1,5-benzodiazepine, melting at about 147°–148° C. This product has the formula

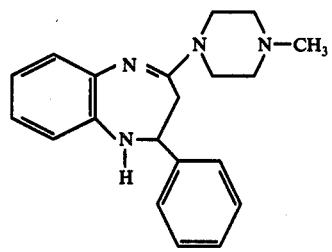

Substitution of an equivalent quantity of the appropriate 2-aryl-4-(1-piperazinyl)-3H-1,5-benzodiazepine fo- 4-(4-methyl-1-piperazinyl)-2-phenyl-3H-1,5-benzodiazepine in the above detailed procedure affords the following compounds:

7-chloro-2,3-dihydro-4-(4-methyl-1-piperazinyl)-2-phenyl-1H-1,5-benzodiazepine;
2,3-dihydro-7,8-dimethyl-4-(4-methyl-1-piperazinyl)-2-phenyl-1H-1,5-benzodiazepine;
2,3-dihydro-4-(4-methyl-1-piperazinyl)-2-phenyl-1H-1,5-benzodiazepine;
2-(p-cholorphenyl)-2,3-dihydro-4-(4-methyl-1-piperazinyl:-1H-1,5-benzodiazepine;
2-(p-fluorophenyl)-2,3-dihydro-4-(4-methyl-1-piperazinyl)-1H-1,5-benzodiazepine;
2,3-dihydro-2-(p-methoxyphenyl)-4-(4-methyl-1-piperazinyl)-1H-1,5-benzodiazepine;
2,3-dihydro-4-(4-methyl-1-piperazinyl)-2-(p-tolyl)-1H-1,5-benzodiazepine; and
2-(p-fluorophenyl)-2,3-dihydro-7,8-dimethyl-4-(4-methyl-1-piperazinyl)-1H-1,5-benzodiazepine.

What is claimed is:
1. A compound of the formula

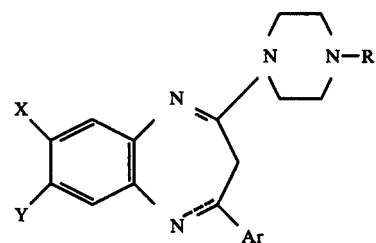

wherein R is hydrogen, alkyl having from 1 to 7 carbon atoms or phenyl; Ar is phenyl, trifluoromethylphenyl or phenyl substituted with 1 or 2 halogen, alkyl having from 1 to 4 carbon atoms or alkoxy having from 1 to 4 carbon atoms; X and Y are each hydrogen, halogen, alkyl having from 1 to 7 carbon atoms or alkoxy having from 1 to 7 carbon atoms; and the dotted line represents a single bond wherein hydrogen is attached to N or a double bond.

2. A compound according to Claim 1 having the formula

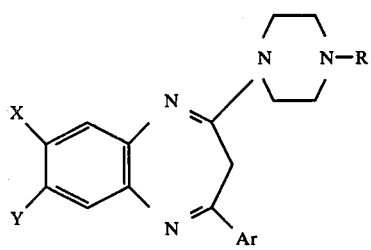

wherein R is hydrogen, alkyl having from 1 to 7 carbon atoms or phenyl; Ar is phenyl, trifluoromethylphenyl or phenyl substituted with 1 or 2 halogen, alkyl having from 1 to 4 carbon atoms or alkoxy having from 1 to 4 carbon atoms; and X and Y are each hydrogen, halogen, alkyl having from 1 to 7 carbon atoms or alkoxy having from 1 to 7 carbon atoms.

3. A compound according to Claim 1 having the formula

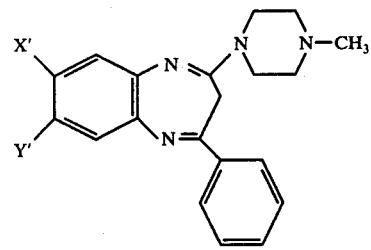

wherein R is hydrogen, alkyl having from 1 to 7 carbon atoms or phenyl; X' is hydrogen, halogen or alkyl having from 1 to 7 carbon atoms; and Y' is hydrogen, halogen or alkyl having from 1 to 7 carbon atoms;

4. A compound according to claim 3 which is 4-(4-methyl-1-piperazinyl)-2-phenyl-3H-1,5-benzodiazepine.

5. A compound according to claim 3 which is 7-chloro-4-(4-methyl-1-piperazinyl)-2-phenyl-3H-1,5-benzodiazepine.

6. A compound according to claim 3 which is 7,8-dimethyl-4-(4-methyl-1-piperazinyl)-2-phenyl-3H-1,5-benzodiazepine.

7. A compound according to claim 3 which is 2-phenyl-4-(4-phenyl-1-piperazinyl)-3H-1,5-benzodiazepine.

8. A compound according to claim 1 having the formula

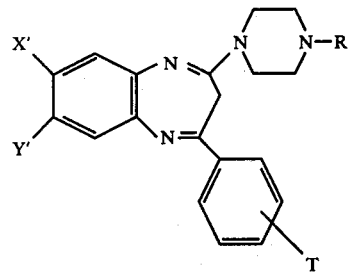

wherein R is hydrogen, alkyl having from 1 to 7 carbon atoms or phenyl; X' is hydrogen, halogen or alkyl having from 1 to 7 carbon atoms; Y' is hydrogen, halogen or alkyl having from 1 to 7 carbon atoms; and T is halogen, alkyl having from 1 to 4 carbon atoms or alkoxy having from 1 to 4 carbon atoms.

9. A compound according to claim 1 having the formula

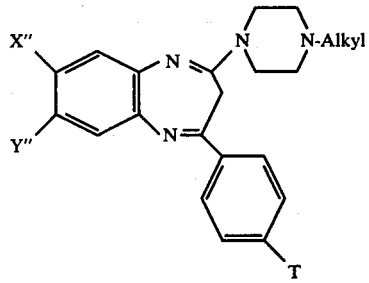

wherein Alkyl contains from 1 to 7 carbon atoms; X" and Y" are each hydrogen or alkyl having from 1 to 7 carbon atoms; and T is halogen, alkyl having from 1 to 4 carbon atoms or alkoxy having from 1 to 4 carbon atoms.

10. A compound according to claim 9 which is 2-(p-chlorophenyl)-4-(4-methyl-1-piperazinyl)-3H-1,5-benzodiazepine.

11. A compound according to claim 9 which is 2-(p-fluorophenyl)-4-(4-methyl-1-piperazinyl)-3H-1,5-benzodiazepine.

12. A compound according to claim 9 which is 4-(4-methyl-1-piperazinyl)-2-(p-tolyl)-3H-1,5-benzodiazepine.

13. A compound according to claim 9 which is 2-(p-methoxyphenyl)-4-(4-methyl-1-piperazinyl)-3H-1,5-benzodiazepine.

14. A compound according to claim 9 which is 2-(p-fluorophenyl)-7,8-dimethyl-4-(4-methyl-1-piperazinyl)-3H-1,5-benzodiazepine.

15. A compound according to claim 1 which is 1,2-dihydro-4-(4-methyl-1-piperazinyl)-2-phenyl-3H-1,5-benzodiazepine.

* * * * *